United States Patent [19]
Rettig et al.

[11] Patent Number: 5,929,317
[45] Date of Patent: Jul. 27, 1999

[54] PROCESS FOR AVOIDING ERROR IN MEASURING OR DETERMINING THE GAS CONSUMPTION OF MATTER

[75] Inventors: Ulrich Rettig, Wielenbach; Willi Fink, Rottenburg, both of Germany

[73] Assignee: WTW Wissenschaftlich-Technische Wekkstatten GmbH, Germany

[21] Appl. No.: 08/812,664

[22] Filed: Mar. 6, 1997

[30] Foreign Application Priority Data

Mar. 8, 1996 [DE] Germany .................... 196 09 071

[51] Int. Cl.$^6$ ...................................... G01N 7/00
[52] U.S. Cl. ............................................. 73/23.2
[58] Field of Search .................. 73/23.2, 34.01, 73/37

[56] References Cited

U.S. PATENT DOCUMENTS

| | | | |
|---|---|---|---|
| 4,608,857 | 9/1986 | Mertens et al. | 73/40.5 |
| 4,762,010 | 8/1988 | Borghard et al. | 73/38 X |
| 5,232,839 | 8/1993 | Eden et al. | 435/39 |
| 5,428,985 | 7/1995 | Kurtz et al. | 73/31.04 X |
| 5,552,114 | 9/1996 | Till | 422/26 |

FOREIGN PATENT DOCUMENTS 0 414 182 A1   2/1991   European Pat. Off. .

OTHER PUBLICATIONS

Michael R. Lindeburg, Eingieering–in–Training Reference Manual, pp. 21–12–21–13, 8th ed., Professional Publicatons, Inc., Belmont, CA. 1992.

*Primary Examiner*—Harshad Patel
*Assistant Examiner*—Robin Clark
*Attorney, Agent, or Firm*—Cantor Colburn LLP

[57] ABSTRACT

A process for avoiding error in determining the gas consumption of a sample located in a closed container. An automatic avoidance of error during the phase of adaptation of the sample to the temperature level in an incubator is achieved by monitoring the container pressure before the beginning of measurement in a test phase, and the measurement values for the measurement of the gas consumption are to be evaluated from the reference time point at which the pressure variation over time in the container lies within a predetermined value range.

12 Claims, No Drawings

PROCESS FOR AVOIDING ERROR IN MEASURING OR DETERMINING THE GAS CONSUMPTION OF MATTER

BACKGROUND OF THE INVENTION

1. Field of the Invention

The present invention concerns a process for avoiding error in measuring or determining the gas consumption of matter, in particular in the case of measuring the biochemical oxygen requirement of a sample located in a closed container.

2. Prior Art

In conventional processes for measuring the biochemical oxygen requirement of a sample located in a closed container, a sample to be measured is placed in a temperature-controlled, respectively air-conditioned, chamber, in particular an incubator, and the container stands open to adjust the sample to the ambient conditions. Then the container was sealed together with the measuring system, and the measurement began. This creates a problem in that the container must be handled to seal the measurement system to the container. It would be beneficial to eliminate excessive handling of the container if not necessary.

SUMMARY OF THE INVENTION

The above-discussed and other drawbacks and deficiencies of the prior art are overcome or alleviated by the process for avoiding error in measuring or determining the gas consumption of matter of the present invention.

An object of the present invention is to ensure a reliable avoidance of error in measuring the gas consumption of matter, in particular in the case of measuring the biochemical oxygen requirement (BOR measurement) of a sample located in a closed container with reduced handling, in particular without having to access again to the container already located in the incubator. This object is achieved through a process for avoiding error in measuring or determining the gas consumption of a sample located in a closed container, wherein the container pressure is monitored in a test phase before obtaining measurement values to be evaluated, and the measurement values for the determination of the gas consumption are evaluated from a reference time point at which the pressure change with respect to time in the container lies within a predetermined value range.

The above-discussed and other features and advantages of the present invention will be appreciated and understood by those skilled in the art from the following detailed description and drawings.

DETAILED DESCRIPTION OF THE INVENTION

In accordance with the invention, the internal pressure in the container is monitored by the measuring device prior to beginning the actual measurement. As a rule, the temperature of the interior of the container adjusts to the temperature in the incubator at this time. For example, a sample which is too cold warms up to the temperature level of the incubator in which the container is located. A sample which is too warm cools down correspondingly. The temperature change of the gas located above the sample creates a corresponding pressure rise/drop. This pressure change due to the temperature change of the gas can inaccurately influence the measurement results and in particular the initial measurement results. Therefore, the measuring device monitors the pressure in the container and begins the measurement only when the pressure change based on the temperature adjustment is insignificant, and therefore the measurement results are no longer falsified significantly. As a rule, the end of the pressure adjustment is recognizable by the fact that the relatively high pressure change over time turns into a small pressure change over time. This moment can be determined by an appropriate choice of a predetermined range of values for the pressure change over time, and can be used for the start of the measurement process or for the beginning of the evaluation of the measurements. It is advantageous to store different predetermined value ranges for different samples (filling levels, container sizes) in a reference value memory of the control device, which then makes it possible to use the measurement device in a sample-specific way. Therefore, the measurement is started when the change in pressure over time lies within the predetermined range of values. In the case of a sample which is too cold, this moment occurs when a pressure rise no longer takes place in the container or the pressure rise, as a result of biochemical processes, turns into a pressure drop, that is, at the inflection point of the pressure curve.

An advantage of the process in accordance with the invention consists in the fact that a reference point with respect to time is defined in the test phase, which point represents the end of the test phase and the beginning of the measurement phase. Measurement values from the measurement phase can then be evaluated. This reference point quite precisely defines the moment at which the biological and physical adjustment of the sample system (sample+container+measurement system) to the environment is substantially complete. Therefore, after the sample is put into the container and connected with the measuring system, it can be sealed immediately and placed in the incubator, without having to have access to the container again later in order to close it. Of course, also it is possible to record the pressure values of the sample system in the incubator simply, e.g. in a measurement value memory and the perform the evaluation in accordance with the present invention after conclusion of the measurement. Also, in this case the pressure behavior is evaluated in accordance with the process described herein, the reference time point specified in the evaluation is defined not at the beginning of the measurement, but at the beginning of the measurement values to be evaluated.

In one advantageous further development of the invention it can be provided that, independent of the measurement system, that is, independent of whether the measurement system is too warm or too cold, an adaptation phase, within which either a measurement or an evaluation of the container pressure takes place, is provided before the test phase. Such an adaptation phase takes place over a time span of 0 to 2 hours and preferably is set at a definite value, e.g. one hour.

Furthermore, it is advantageous if the test phase is adjustable to a maximum value, e.g. 2.5 hours. In this way the testing of the pressure change is limited to a sensible total time after the adaptation phase.

Preferably the pressure monitoring during the test phase is performed at time intervals of 0 to 60 minutes, which is advantageous when a battery or accumulator-operated measurement process is used. The time interval is set to a suitable value, which is based on the usual duration of the test phase. Time intervals between 10 minutes and 50 minutes are preferred. After a time interval there is a pressure comparison with the last measurement value stored. If the current pressure (measurement) value is greater than the previous pressure value stored, the zero point of the pressure measurement system is set to the current pressure value, and a new time interval is started. The actual measurement is started only if the pressure after the expiration of the time interval is smaller than or equal to the last zero point set. The last zero point of the measurement system is used as a starting value for the automatic measurement.

During the currently running measurement phase, the measurement value formation is taken in time intervals of 10 seconds to 24 hours. The time intervals in a battery or accumulator-operated measurement device preferably lie between 12 and 24 hours.

In a further embodiment with external data evaluation, the measurement value formation preferably can be made between 5 and 60 minutes.

In one embodiment, in which the measurement system is designed as a pure pressure acquisition system, the determination of the starting point for measurement values is performed after the expiration of the entire running time of the pressure value acquisition. The determination of the starting point for actual measurement values is performed in the manner described above in the case of the immediate data evaluation. The transmission of measurement values between the measuring system and the evaluating device takes place either off-line (e.g. after the conclusion of the measurements from the memory of the measuring system) or on-line (during measurement via wire, radio, IR, ultrasound, or inductive connection).

The process for avoiding error in measuring the gas consumption of matter is suited for all forms of measurements in which a substance in a closed container causes a reduction of the pressure, respectively partial pressure of a specific gas in the container. In particular, this process is suited for the measurement of the biochemical oxygen requirement. At the beginning of the measurement the current pressure value is set as the zero value for the following measurement. Previous biological and physical adjustments of the sample system thus are not considered it the evaluation of the pressure values measured for the BOR measurement.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A process for avoiding error in measuring or determining gas consumption of a sample located in a sealed container, comprising:

placing a measurement system in connection with a container:

sealing the container;

placing the sealed container and measurement system in a temperature-controlled chamber;

initiating a test phase for monitoring the pressure in the container;

initiating a measurement phase for measuring gas consumption from a reference time point when the pressure change with respect to time lies within a predetermined value range.

2. A process in accordance with claim 1, wherein the measurement phase comprises:

obtaining measurement values to be evaluated; and evaluating the measurement values from said reference time point.

3. A process in accordance with claim 2, wherein the measurement values for the determination of the gas consumption are evaluated after the pressure in the container begins to drop.

4. A process in accordance with claim 1, wherein the time for the test phase is limited to a maximum value, after which the measurement results for determining the gas consumption are evaluated, independent of the pressure behavior in the container.

5. A process in accordance with claim 3, wherein the time for the test phase is limited to a maximum value, after which the measurement results for determining the gas consumption are evaluated, independent of the pressure behavior in the container.

6. A process in accordance with claim 4, wherein a maximum value for the test phase is in the range of 0 minutes to 2.5 hours.

7. A process in accordance with claim 1, further comprising:

initiating an adaption phase prior to the test phase, wherein the adaption phase has a definite time span and during the adaption phase no pressure evaluation or pressure measurement occurs.

8. A process in accordance with claim 7, wherein the time span for the adaptation phase is in the range of 30 minutes to 2 hours.

9. A process in accordance with claim 1, wherein the pressure is recorded and evaluated at specific intervals during the measurement phase.

10. A process in accordance with claim 1, wherein during the test phase a pressure measurement takes place at intervals with a time span in the range of 10 seconds to 60 minutes.

11. A process in accordance with claim 2, wherein the pressure of the test phase is evaluated only during the measurement in an incubator, and the determination of the reference time point occurs after the measurement of the pressure.

12. A process in accordance with claim 2, wherein the evaluation takes place in a separate evaluation device outside the incubator after conclusion of the measurements.

* * * * *